United States Patent [19]

Smith

[11] Patent Number: 5,753,451
[45] Date of Patent: May 19, 1998

[54] PROCESS FOR DETERMINING SPECIFIC GRAVITY OF ADULTERANTS IN URINE EMPLOYING AN AUTOMATIC ANALYZER

[75] Inventor: Jack V. Smith, St. Petersburg, Fla.

[73] Assignee: Chimera Research & Chemical, Inc., Tampa, Fla.

[21] Appl. No.: 786,118

[22] Filed: Jan. 17, 1997

Related U.S. Application Data

[63] Continuation of Ser. No. 497,641, Jun. 30, 1995, abandoned, which is a continuation-in-part of Ser. No. 276,502, Jul. 18, 1994, abandoned, which is a continuation of Ser. No. 700,713, May 16, 1991, abandoned.

[51] Int. Cl.[6] .................................................. C12Q 1/58
[52] U.S. Cl. ................................ 435/12; 422/56; 73/32 R
[58] Field of Search ................................ 435/12; 422/56; 436/2, 24, 164; 73/32 R

[56] References Cited

U.S. PATENT DOCUMENTS

| | | | |
|---|---|---|---|
| 4,318,709 | 3/1982 | Falb et al. | 23/230 R |
| 4,376,827 | 3/1983 | Stiso et al. | 436/2 |
| 4,590,800 | 5/1986 | Shimoda | 73/449 |
| 5,179,027 | 1/1993 | Fisher | 436/56 |
| 5,302,531 | 4/1994 | Bauer | 436/74 |
| 5,320,969 | 6/1994 | Bauer et al. | 436/84 |
| 5,350,694 | 9/1994 | Zimmerle | 436/2 |

OTHER PUBLICATIONS

Mikkelsen S., Identification of Substances Interfering With Illicit Drug Testing, AFIT/CI/NR–88–116 Masters Thesis, 1988.

*Primary Examiner*—Ralph Gitomer
*Attorney, Agent, or Firm*—Larson & Larson, P.A.; Herbert W. Larson

[57] ABSTRACT

An automatic analyzer is used to determine out of range specific gravity of adulterants in a urine sample. An aliquot of the urine is mixed with a buffer and ion detector and thereafter with a polymer activator for ion detection. The mixture is analyzed by setting a spectrophotometer in the automatic analyzer at about 600 nanometers, setting the calibrating value for specific gravity at 1.000 and 1.0500 and reading a color change to determine the presence of adulterants.

7 Claims, No Drawings

PROCESS FOR DETERMINING SPECIFIC GRAVITY OF ADULTERANTS IN URINE EMPLOYING AN AUTOMATIC ANALYZER

PRIOR APPLICATIONS

This application is a continuation from Ser. No. 08/497,641, filed Jun. 30, 1995, which is a continuation-in-part from application Ser. No. 08/276,502, filed Jul. 18, 1994, which is a continuation from Ser. No. 07/700,713, filed May 16, 1991, all now abandoned.

BACKGROUND OF THE INVENTION

This invention relates to a single reagent system for use in determining the specific gravity in urine, or other fluids, being screened for drugs of abuse. This invention is particularly useful in automated analyzers used in screening for drugs of abuse.

As the use of illicit drugs in the workplace, public transportation, professional and amateur athletics and the like has grown, public concern for the health and safety of individuals, as well as concern for the negative impact of such drug use on productivity of industry, and its inherent economic impact, and the general well being and health of the community at large has grown as well. Such concern has led to the use of analysis of urine as a way to detect and deter drug use. Such testing for drugs of abuse in industry, as for prospective and current employees, military personnel, transportation employees, professional and amateur atheletes, as well as people under supervision of the criminal justice system, has become a relative common occurence.

Because of the intrusive nature of such testing, commonly performed by examining a urine sample, the testing procedure must withstand vigorous scrutiny. As a positive test result of screening for drugs of abuse may have serious impact on the life of a person being tested, the incentive for the drug user to alter the test specimen is high. The users of drugs of abuse have developed a number of ways to adulterate the collected specimen, thus attempting to produce a false negative result in the drug screening test being conducted.

A user of drugs of abuse may attempt to affect the test results, thus producing a false negative test result, or upon occasion, a false positive result, as by: a) dilution—efforts to reduce the drug concentration in the urine sample; b) substitution—substitution of liquids such as clean (that is, drug-free) urine, soda, tea, apple juice for the drug-containing sample; or c) adulteration—addition to the urine specimen of foreign material in an attempt to invalidate the test.

Illicit drug users have learned to falsify urine screen tests by in vitro adulteration of the urine sample by the addition of several readily available agents, including household products, among others, NaCl, soap, such as hand or dish soap, bleach, vinegar, Drano Pipe Cleaner, $NaHCO_3$, Visine eye drops, GOLD SEAL TEA (available in natural food stores), or $H_2O_2$.

Additionally, users of drugs of abuse may eliminate some drugs more rapidly from their bodies by altering their urinary pH. Abusers of phencyclidine or amphetamines may be treated with $NH_4Cl$ to hasten detoxification, thus increasing the rate at which substances (phencyclidine or amphetamines) are eliminated from their bodies. This treatment with $NH_4Cl$ also results in lowering the pH of the user's urine.

While the use of some in vitro adulterants can be eliminated by the direct observation of the test subject during the collection process, such direct observation is often deemed unacceptable. In vivo adulterants represent an additional burden to the screening processor because they are consumed by the drug user several hours or days prior to screening of the sample, and can be detected only by laboratory means.

Such adulteration can affect all three commonly used methods for drugs of abuse, namely: fluorescent polarization immunoassay (FPIA), radioimmunoassay (RIA), and enzyme immunoassay (EMIT or EIA). Consequently, clinical chemistry literature recommends that testing for drugs of abuse in urine samples include testing for adulterants to identify urine samples which have been adulterated. See Mikkelsen and Ash, "Adulterants Causing False Negatives In Illicit Drug Testing", *Clin. Chem.* 34/11, 2333–2336 (1988); and Warner, "Interference of Common Household Chemicals In Immunoassay Methods For Drugs Of Abuse", *Clin. Chem.* 35/4, 648–651 (1989).

Accordingly, a need exists for providing an easy and convenient manner by which to make determination of the presence of adulterants in urine samples which are being tested for drugs of abuse. A further need exists for a convenient manner by which such determinations may be made in conjunction with an automatic analyzing process for drugs of abuse.

SUMMARY OF THE INVENTION

The present invention relates to a single channel reagent to detect simultaneously multiple levels of specific gravity in urine or other fluids. This reagent is designed to be used on automated analyzers used for drugs of abuse testing.

The purpose of the reagent is to facilitate the conducting of testing for specific gravity simultaneously while conducting drug tests on the same automatic analyzer. Specifically, if the specific gravity of the urine, or other sample fluid being tested, is out of the normal range, that is, greater than 1.030 specific gravity units or less than 1.005 specific gravity units, such variation from the normal range will cause false negative readings, when tested by a common drug-screening method, namely, EIA (enzyme immunoassay) in testing for drugs of abuse, such as: methadone, opiate, THC, barbituate, PCP, amphetamine, benzodiazepine, cocaine, propoxyphene. For example, the adulteration of a urine sample with a common agent such as table salt, NaCl, will result in a change in the specific gravity of the urine sample.

It is helpful to note that upon occasion, abnormally high amounts of urinary constituents, as excreted by the body, can cause an increase in specific gravity values. Also, the disease of diabetes insipidus is characterized by large urine volumes of low specific gravity, usually between the values of 1.001 and 1.003.

Use of the reagent of this invention permits the technician conducting the test to halt the testing process, or assay, as soon as the out-of-range specific gravity determination is made. The ability to terminate the screening process by ascertaining that the specific gravity of the sample is out of range, and therefore presumably adulterated, would result in reduced technician's efforts and time, providing an economic savings to the testing laboratory. Furthermore, the early interruption and cessation of the automated screening process may facilitate earlier obtention of a substitute specimen from the person being tested, providing more accurate determinations to the agency which had determined the original necessity for the test.

The use of the instant reagent system permits the determination of the specific gravity of the testing sample to be done by the automated substance abuse testing program, rather than the relatively cumbersome methods of hand-held methods of testing for adulteration, such as the use of pH test (litmus) paper, which must be dipped in the urine, by pH metering or other manual methods.

The instant reagent system comprises an aqueous solution of different specific gravity indicators that effect a color change, depending on the specific gravity of the urine, or other sample fluid being tested. The reagent is based on an indicator principal (redox) which gives a broad range of colors throughout the urinary specific gravity range, normally in the range of 1.005 to 1.030, but usually remaining between 1.010 and 1.025. A sample of urine is mixed with the reagent in a specific ratio, and the mixture of urine and reagent will exhibit a color change, depending on the specific gravity of the urine. The color change results in a change in the light absorbance, which may be detected by a spectrophotometer at 600 nanometers.

DETAILED DESCRIPTION OF THE INVENTION

The specific gravity reagent of the instant invention comprises an aqueous solution of a divalent buffer, which is mixed with the urine or other fluid sample to be tested. The mixture of the fluid sample with the divalent buffer, which serves as a reaction stabilizer, and which also includes an activator, or ion detector, hereinafter referred to as R1 Diluent, is then mixed with a second aqueous solution, referred to hereinafter as R2 Color, which includes a particular polymer, which functions as an activator for ion detection, and color indicator. The entire mixture is then inserted into the instrument, and the absorbance read for comparison against known standards.

The formulations for R1 Diluent and R2 Color are prepared as follows:

R1 DILUENT is prepared as follows:

10.0 g sodium thiosulfate 100 ml isopropanol 6.8 g potassium phosphate monobasic ($KH_2PO_4$)

7.1 g sodium phosphate dibasic 12-hydrate $Na_2PO_4$)

0.1 g sodium azide 1.0 ml Triton X-100 octoxynol 1.0 ml Brij 35 solution, 30% w/v (polyoxyethylene 23 lauryl ether)

The ingredients are mixed together, and the pH of the solution is adjusted to between 6.85–6.90 with sodium hydroxide or lactic acid, as appropriate. The solution is then brought to 1.1 liter with reagent grade distilled water.

R2 COLOR

A solution, known hereinafter as R2 COLOR CONCENTRATE, is prepared according to the following formulation:

30.0 g methyl vinyl ether/maleic anhydride 750 ml isopropanol 250 ml Reagent grade distilled water.

The solution is mixed thoroughly, for 48 to 72 hours, or until compound goes into solution.

R2 COLOR is prepared as follows:

175 ml R2 COLOR CONCENTRATE 1.5 g Bromthymol Blue (or other indicator as indicated in list A below, or mixture of color indicators)

6.0 ml Brij 35 solution, 30% w/v (polyoxyethylene 23 lauryl ether)

1.0% Isopropanol

The pH of the solution is adjusted to 8.0 with sodium hydroxide or lactic acid, as appropriate. The R2COLOR solution is brought to a quantity of 6.0 L with reagent grade distilled water.

A - Indicators for R2COLOR 1.5 g Bromthymol Blue
1.5 g alizarin yellow R
1.5 g Tetrabromphenol Blue
1.5 g Brom-chlorphenol Blue
1.5 g Thymol Blue
1.5 g Metacresol Purple
1.5 g Phenolthalein
1.5 g thymolphthalein
1.5 g o-cresolphthalein
1.5 g tropaeolin 000 no. 1
1.5 g cresol red
1.5 g neutral red
1.5 g p-nitrophenol
1.5 g dibromophenol-tetrabromophenol-sulfonphthalein
1.5 g bromphenol red
1.5 g bromcresol purple
1.5 g azolitmin
1.5 g benzoyl auramine G
1.5 g chlorphenol red
1.5 g litmus
1.5 g lacmoid
1.5 g methyl red
1.5 g 2.5 - dinitrophenol
1.5 g 2.4 - dinitrophenol
1.5 g bromalsol green
1.5 g sodium alizarinsulfonate
1.5 g napthyl red
1.5 g p-ethoxchrysoidine
1.5 g methyl orange
1.5 g congo red
1.5 g bromphenol blue
1.5 g methyl yellow
1.5 g quinaldine red
1.5 g tropaelin 00
1.5 g p-xylenol blue
1.5 g metanil yellow
1.5 g methyl violet (Note that the method of preparation of the R2COLOR solution is the same, with any of the indicators in list A.)

The reagent system of the instant invention is intended for use on automatic analyzers, such as enzyme immunoassay analyzers (EMIT), such as Olympus AU 5000 series, Monarch, Hitachi 700 series, among others. On these instruments, the reagent is used in the following manner: 5 µL of urine sample is placed in a sample tube and mixed with 50 µL of R1 DILUENT. This mixture is then mixed with 300 µL of R2 COLOR. The instrument spectrophotometer is set at 600 nm, and the calibrator values of the instrument are set at a normal high value of 1.0300 and the normal low value set at 1.0050. The absorbance of the sample is then measured.

In the instant invention, when urine which has been adulterated, resulting in a change in the specific gravity, is mixed with the reagent system in the prescribed ratio, the indicator will cause the sample mixture to change color, depending on the specific gravity (ionic strength) of the solution. Such indication may be seen in a manual inspection, but is especially intended for use in automatic analysis, such as those which employ spectophotometric means of inspection.

Specifications for running the urine samples through three specific instruments, of the enzyme immunoassay type (EMIT) Olympus, Hitachi and Monarch, are listed below. The settings are intended as guidelines, and are set forth with the understanding that those skilled in the art would recognize that such parameters will vary from instrument to instrument. The suggested specifications are as follows:

Parameter Settings for Olympus AU5000

1. Turn on yes/no—yes

Sample vol.: 05 µL

R1 DILUENT vol.: 50 µL

R2 COLOR vol.: 300 µL

2. Activate—W3

R1—yes

R2—yes

Wavelength 1: 600 nm.

Wavelength 2: 000 nm

Curve (slope): —

Measuring points (photo station)

start at 0 end at 3

11. Normal High Value-1.0300

Normal Low Value-1.0050

12. O.D. range-2.5000 to −2.0000

Calibration method (TYPE): AA

1) Concentration 1=1.005

2) Concentration 2=1.030

Note: Group Number (#) Blank (to be determined by testing facility), Cal 1 concentration—1.005Group Number (#) Blank, Cal 2 concentration—1.030

| Parameter Settings for Monarch | |
|---|---|
| Identification Parameters: | |
| Test code | 116 |
| Test name | SG |
| Test mnemonic | SG |
| Optical mode | Absorbance |
| Response algorithm | Final point |
| Result algorithm | Linear |
| Loading Parameters: | |
| Loading type | Load Analyze |
| Reagent blank | Off |
| Reference type | Diluent |
| Calibrator type | Test specific |
| Sample volume | 4 µL |
| Sample diluent | 5 µL |
| Reagent diluent | 10 µL |
| 1st reagent | 175 µL |
| 2nd reagent | 40 µL |
| 1st rgt bar code | 1 k |
| Data Acquisition Parameters: | |
| Analysis type | Mix run |
| Temperature | 25 C |
| Delay time | 30 sec. |
| Interval time | 30 sec |
| No. of data points | 1 |
| Filter 1 | 600 nm |
| Filter 2 | 600 nm |
| Monochromator 1 | 600 nm |
| Monochromator 2 | 600 nm |
| Compatibility | None |
| Data Integrity Parameters: | |
| Integrity tests | Normal range |

-continued

| Parameter Settings for Monarch | |
|---|---|
| Lower limit | 1.005 |
| Upper limit | 1.030 |
| Data Fit Parameters: | |
| Calibrator 1 | 1.005 |
| Calibrator 2 | 1.030 |
| Correction mode | none |
| Units | none |
| No. of decimal places | 4 |
| Calculated Parameters: | |
| Data edited | (date) |
| Time edited | (time) |
| Not calibrated run time | 30 sec. |

It is recommended that calibrator values for the automated analyzers be set at values of 1.005 and 1.030, with the instrument set to flag values at or below 1.003, as well as values at or above 1.035.

Example

Sixty urine specimens were assayed for specific gravity using the reagent system of the invention on the Hitachi 717 by an independent laboratory. The assay was compared to the reference assay (refractometer) using correlation and regression analysis, along with estimated standard of error of the regression. Also the Ames Dipstick method was used with the reference method. The assay was conducted in conjunction with an assay to evaluate automated pH screening, using pH reagents of the inventor of the instant specific gravity reagent system.

The specific gravity reagent of the instant invention was used, per manufacturer's instructions in the Hitachi assay.

The laboratory used the BIGRESS program (Bivarate Regression) on the EXPLORE (statistical software package) to conduct the statistical analysis on the results.

The specific gravity values for 60 urine samples measured by the Hitachi/reagent method, the reference/refractometer method and the Ames dipstick method are as follows:

| Sample # | Hitachi Value | Reference Value | Dipstick Value |
|---|---|---|---|
| 1 | 1.004 | 1.013 | 1.020 |
| 2 | 1.010 | 1.011 | 1.020 |
| 3 | 1.031 | 1.028 | 1.030 |
| 4 | 1.014 | 1.020 | 1.020 |
| 5 | 1.022 | 1.033 | 1.030 |
| 6 | 1.017 | 1.023 | 1.030 |
| 7 | 1.013 | 1.017 | 1.020 |
| 8 | 1.004 | 1.008 | 1.010 |
| 9 | 1.009 | 1.018 | 1.030 |
| 10 | 1.013 | 1.021 | 1.030 |
| 11 | 1.007 | 1.022 | 1.020 |
| 12 | 1.015 | 1.021 | 1.030 |
| 13 | 1.018 | 1.020 | 1.030 |
| 14 | 1.017 | 1.030 | 1.030 |
| 15 | 1.006 | 1.013 | 1.020 |
| 16 | 1.019 | 1.024 | 1.030 |
| 17 | 1.021 | 1.025 | 1.030 |
| 18 | 1.011 | 1.016 | 1.020 |
| 19 | 1.005 | 1.006 | 1.020 |
| 20 | 1.009 | 1.010 | 1.030 |
| 21 | 1.011 | 1.016 | 1.030 |
| 22 | 1.019 | 1.024 | 1.020 |
| 23 | 1.009 | 1.016 | 1.020 |
| 24 | 1.005 | 1.011 | 1.015 |
| 25 | 1.006 | 1.005 | 1.015 |

-continued

| Sample # | Hitachi Value | Reference Value | Dipstick Value |
|---|---|---|---|
| 26 | 0.997 | 1.017 | 1.020 |
| 27 | 1.006 | 1.013 | 1.020 |
| 28 | 1.006 | 1.008 | 1.030 |
| 29 | 1.012 | 1.026 | 1.030 |
| 30 | 1.016 | 1.020 | 1.020 |
| 31 | 1.011 | 1.031 | 1.030 |
| 32 | 1.020 | 1.028 | 1.030 |
| 33 | 1.027 | 1.028 | 1.025 |
| 34 | 1.016 | 1.019 | 1.030 |
| 35 | 1.021 | 1.023 | 1.030 |
| 36 | 1.022 | 1.019 | 1.020 |
| 37 | 1.008 | 1.010 | 1.030 |
| 38 | 1.020 | 1.018 | 1.025 |
| 39 | 1.007 | 1.013 | 1.025 |
| 40 | 1.012 | 1.018 | 1.030 |
| 41 | 1.002 | 1.022 | 1.020 |
| 42 | 1.022 | 1.024 | 1.030 |
| 43 | 1.027 | 1.027 | 1.030 |
| 44 | 1.029 | 1.024 | 1.030 |
| 45 | 1.012 | 1.020 | 1.020 |
| 46 | 1.006 | 1.019 | 1.030 |
| 47 | 1.021 | 1.024 | 1.020 |
| 48 | 1.003 | 1.015 | 1.025 |
| 49 | 1.002 | 1.017 | 1.025 |
| 50 | 1.000 | 1.017 | 1.025 |
| 51 | 1.007 | 1.012 | 1.025 |
| 52 | 1.023 | 1.024 | 1.025 |
| 53 | 1.012 | 1.023 | 1.030 |
| 54 | 1.026 | 1.030 | 1.030 |
| 55 | 1.013 | 1.017 | 1.030 |
| 56 | 1.012 | 1.012 | 1.030 |
| 57 | 1.014 | 1.016 | 1.030 |
| 58 | 1.014 | 1.015 | 1.030 |
| 59 | 1.005 | 1.007 | 1.025 |
| 60 | 1.016 | 1.022 | 1.030 |

After correlating the data, 3% (or 2 out of 60 specimens) had values less than 1.003, suggesting confirmation of the results with a refractometer.

Using the above-noted software for the statistical analysis, laboratory noted that the mean results of the Hitachi method, using the instant reagent, would not vary more than +/−.0014, suggesting a very high level of reliabilty.

It will be understood that the embodiments described in the instant application are merely exemplary and that a person skilled in the art may make variations and modifications without departing from the spirit and scope of the invention. All such modifications and variations are to be included within the scope of the invention as defined in the appended claims:

I claim:

1. A process employing an automatic analyzer to determine specific gravity outside of normal range on a urine sample, comprising:

(a) mixing an aliquot of the urine sample with a divalent buffer in an aqueous solution containing at lest 0.1% by weight surfactants to form a first mixture, (b) thereafter, mixing the first mixture with methyl vinyl ether/maleic anhydride, at least 0.1% by weight surfactants and a color indicator to form a second mixture, (c) placing the second mixture into a cuvette within the automatic analyzer, (c) setting a spectrophotometer in the automatic analyzer for reading at about 600 nanometers, (e) setting a calibrating value for specific gravity in the automatic analyzer between 1.000 and 1.0500, and (f) reading a color change to determine a presence of an out of normal range specific gravity below 1.005 or above 1.030 in the urine sample with a sensitivity of ± 0.001.

2. The process according to claim 1 wherein the first mixture is obtained by mixing with the urine, an aqueous solution of potassium phosphate, sodium phosphate, sodium azide, and the surfactant octoxynol.

3. the process according to claim 1 wherein at least one surfactant added to the first mixture is polyoxyethylene 23 lauryl ether.

4. The process according to claim 1 wherein the pH of the first mixture is adjusted to between 6.85 and 6.90.

5. The process according to claim 1 wherein isopropanol and water are added to the second mixture in step (b).

6. The process according to claim 5 wherein the color indicator is bromethymol blue and a surfactant added is polyoxyethylene 23 lauryl ether.

7. The method of quantitatively determining out of normal range specific gravity of a urine sample comprising:

(a) mixing the urine sample with a divalent buffer in an aqueous solution containing at least 0.1% by weight surfactants to form a first mixture, (b) mixing the first mixture with methyl vinyl ether/ maleic anhydride, at least 0.1% by weight surfactants and a color indicator to form a second mixture.

(c) placing the second mixture into a cuvette within an automatic analyzer, (d) setting a spectrophotometer in the automatic analyzer for reading at about 600 nanometers, (e) setting a calibrating value for specific gravity in the automatic analyzer between 1.000 and 1.0500, and (f) reading a color change to quantitatively determine a presence or absence of an out of normal range specific gravity below 1.005 or above 1.030 in the urine sample with a sensitivity of ±0.001.

* * * * *